United States Patent
Segawa et al.

(10) Patent No.: US 10,278,408 B2
(45) Date of Patent: May 7, 2019

(54) TRANSPARENT AND TRANSLUSCENT LIQUID FILLED CANDY; PROCESS OF MAKING THEREOF; SUGAR-FREE LIQUID EDIBLE COMPOSITION; AND USE THEREOF

(71) Applicant: INTERCONTINENTAL GREAT BRANDS LLC, East Hanover, NJ (US)

(72) Inventors: Hiroshi Segawa, Tokyo (JP); Yoshimitsu Yamakura, Tokyo (JP); Takaya Koseki, Tokyo (JP); Yuzuru Mitsui, Tokyo (JP); Koichi Enomoto, Tokyo (JP)

(73) Assignee: INTERCONTINENTAL GREAT BRANDS LLC, East Hanover, NJ (US)

( * ) Notice: Subject to any disclaimer, the term of this patent is extended or adjusted under 35 U.S.C. 154(b) by 521 days.

(21) Appl. No.: 14/774,411

(22) PCT Filed: Mar. 27, 2014

(86) PCT No.: PCT/US2014/031946
§ 371 (c)(1),
(2) Date: Sep. 10, 2015

(87) PCT Pub. No.: WO2014/160823
PCT Pub. Date: Oct. 2, 2014

(65) Prior Publication Data
US 2016/0029658 A1     Feb. 4, 2016

Related U.S. Application Data

(60) Provisional application No. 61/806,609, filed on Mar. 29, 2013.

(51) Int. Cl.
| A23G 3/54 | (2006.01) |
| A23G 1/54 | (2006.01) |
| A23G 3/38 | (2006.01) |
| A23G 3/40 | (2006.01) |
| A23G 4/20 | (2006.01) |
| A61K 9/00 | (2006.01) |

(52) U.S. Cl.
CPC ............... *A23G 3/545* (2013.01); *A23G 1/54* (2013.01); *A23G 3/38* (2013.01); *A23G 3/40* (2013.01); *A23G 3/54* (2013.01); *A23G 4/20* (2013.01); *A61K 9/0056* (2013.01); *A23V 2002/00* (2013.01)

(58) Field of Classification Search
CPC ... A23G 1/54; A23G 3/34; A23G 3/38; A23G 3/40; A23G 3/54
USPC ........................................................ 426/103
See application file for complete search history.

(56) References Cited

U.S. PATENT DOCUMENTS

| 4,032,661 | A | | 6/1977 | Rowsell et al. | |
| 4,136,163 | A | | 1/1979 | Watson et al. | |
| 4,178,459 | A | | 12/1979 | Watson et al. | |
| 4,230,688 | A | | 10/1980 | Rowsell et al. | |
| 4,260,596 | A | * | 4/1981 | Mackles ............. | A61K 9/0056 424/440 |
| 4,296,255 | A | | 10/1981 | Roswell et al. | |
| 4,459,425 | A | | 7/1984 | Amano et al. | |
| 4,861,600 | A | | 8/1989 | Chisari et al. | |
| 4,975,287 | A | | 12/1990 | Zibell et al. | |
| 5,009,893 | A | | 4/1991 | Cherukuri et al. | |
| 5,266,592 | A | | 11/1993 | Grub et al. | |
| 5,425,957 | A | | 6/1995 | Gaim-Marsoner | |
| 5,436,013 | A | | 7/1995 | Synosky et al. | |
| 5,629,042 | A | * | 5/1997 | Serpelloni ............. | A23G 3/04 426/548 |
| 5,698,181 | A | | 12/1997 | Luo | |
| 6,277,385 | B1 | | 8/2001 | Luke | |
| 6,280,762 | B1 | * | 8/2001 | Bealin-Kelly ........ | A61K 9/0056 424/439 |
| 6,395,316 | B1 | | 5/2002 | Leas et al. | |
| 6,558,727 | B2 | * | 5/2003 | Degady ................ | A23G 3/125 425/126.2 |
| 6,592,884 | B2 | | 7/2003 | Hofmann et al. | |
| 6,627,233 | B1 | | 9/2003 | Wolf et al. | |
| 6,764,707 | B1 | | 7/2004 | Masui et al. | |
| 7,030,273 | B1 | | 4/2006 | Sun | |
| 7,189,760 | B2 | | 3/2007 | Erman et al. | |
| 2001/0048965 | A1 | | 12/2001 | Cherukuri | |
| 2003/0026826 | A1 | | 2/2003 | Cherukuri et al. | |
| 2003/0215553 | A1 | * | 11/2003 | Ribadeau-Dumas | A23G 3/0006 426/548 |
| 2004/0101615 | A1 | | 5/2004 | Barker et al. | |
| 2005/0002993 | A1 | * | 1/2005 | Goggin ................ | A61K 9/0056 424/440 |

(Continued)

FOREIGN PATENT DOCUMENTS

| CN | 106805218 A * | 6/2017 |
| EP | 0393327 A2 | 10/1990 |

(Continued)

OTHER PUBLICATIONS

Beneo-Palatinit.Com Web Pages, Food Ingredients, Isomalt, 2010, 3 pages.
International Search Report for Application No. PCT/US2014031946, filing date Mar. 27, 2014, dated Jan. 9, 2015, 8 pages.
Kirk-Othmer Encyclopedia of Chem. Tech. 4th Ed. vol. 1, p. 492-494, 1991.

(Continued)

*Primary Examiner* — Jyoti Chawla
(74) *Attorney, Agent, or Firm* — Cantor Colburn LLP (57) ABSTRACT

Disclosed is confectionery having a transparent or translucent hard candy shell and a water-in-oil emulsion centerfill. Also disclosed is a sugar-free liquid edible composition and use in confectionery products.

26 Claims, 6 Drawing Sheets

(56) References Cited

U.S. PATENT DOCUMENTS

| | | |
|---|---|---|
| 2005/0222256 A1 | 10/2005 | Erman et al. |
| 2005/0265930 A1 | 12/2005 | Erman et al. |
| 2006/0051456 A1 | 3/2006 | Cadbury Schweppes |
| 2007/0031561 A1 | 2/2007 | Lakkis et al. |
| 2009/0092565 A1 | 4/2009 | Koyoma et al. |
| 2010/0166914 A1* | 7/2010 | Herron .................. A23G 1/48 426/61 |
| 2011/0256072 A1 | 10/2011 | Tanaka et al. |
| 2011/0256271 A1* | 10/2011 | Bhattacharya ....... A23G 3/0046 426/103 |
| 2014/0127353 A1 | 5/2014 | Kamakura et al. |
| 2016/0000114 A1 | 1/2016 | Segawa et al. |
| 2016/0029658 A1 | 2/2016 | Segawa et al. |

FOREIGN PATENT DOCUMENTS

| | | | |
|---|---|---|---|
| EP | 0696449 | A2 | 2/1996 |
| EP | 2457449 | A1 | 5/2012 |
| EP | 2692240 | A1 | 2/2014 |
| WO | 9206943 | A1 | 4/1992 |
| WO | 9517829 | A1 | 7/1995 |
| WO | 1998047484 | A1 | 10/1998 |
| WO | WO 9847482 A1 * | 10/1998 | ........... A61K 9/0056 |
| WO | 2002056698 | A1 | 7/2002 |
| WO | 2004096184 | A1 | 11/2004 |
| WO | 2007037781 | A2 | 12/2005 |
| WO | 2006125334 | A1 | 11/2006 |
| WO | 2008030274 | A1 | 3/2008 |
| WO | 2009090416 | A1 | 7/2009 |
| WO | 2011010723 | A1 | 1/2011 |
| WO | 2011137329 | A2 | 11/2011 |
| WO | 2012024469 | A1 | 2/2012 |

OTHER PUBLICATIONS

Written Opinion for Application No. PCT/US2014031946, filed Mar. 27, 2014, dated Jan. 9, 2015, 9 pages.

Extended EP Search Report; Application No. 15180352.5; dated Feb. 3, 2016; 11 pages.

* cited by examiner

FIG. 6

TRANSPARENT AND TRANSLUSCENT LIQUID FILLED CANDY; PROCESS OF MAKING THEREOF; SUGAR-FREE LIQUID EDIBLE COMPOSITION; AND USE THEREOF

CROSS REFERENCE TO RELATED APPLICATIONS

This application is a National Stage application of PCT/US2014/031946, filed Mar. 27, 2014, which claims the benefit of U.S. Provisional Application No. 61/806,609, filed Mar. 29, 2013, both of which are incorporated by reference in their entirety herein.

FIELD

This disclosure generally relates to transparent or translucent confectionery having multiple phases, multiple components, and multiple textures; and generally relates to sugar-free liquid edible compositions.

BACKGROUND

Hard boiled candies are known hard, solid confectionery in an essentially amorphous or "glassy" form and containing a low moisture content. Sugar-based hard boiled candies are made by boiling a mixture of sugar, glucose syrup and water to moisture content of around three percent. Sugar-free hard boiled candies can be prepared by boiling a mixture of a sugar polyol and water, optionally with a sugar polyol syrup.

The type of bulk sweetener used to prepare the hard boiled sweet has an effect on the stability of the final hard candy product. Less hygroscopic materials resist the absorption of moisture from the surroundings which can lead to crystal formation, graining, and softening of the product. When the hard boiled candy is formulated with a centerfill material, the properties of the center-fill can affect the stability of the hard boiled candy portion and correspondingly the overall product.

There remains a need in the art to provide liquid center-filled hard boiled candies having stability during storage such that the center-fill does not leak from the product while at the same time providing the consumer with the contrast of a solid candy and a liquid mouthfeel.

SUMMARY

In an embodiment, a confectionery product comprises a translucent hard candy shell comprising a first flavorant, and a liquid center composition wherein the liquid center composition is a water-in-oil emulsion comprising a second flavorant and a colorant, the liquid center composition is completely surrounded by and is visible through the hard candy shell; wherein the liquid center composition has a contact angle of less than 80 degrees on a gelatin coated surface. The confectionery product can be prepared by a deposit molding process.

In an embodiment, a package comprises a plurality of deposited confectionery products, the deposited confectionery comprising a translucent hard candy shell comprising a first flavorant, and a liquid center composition wherein the liquid center composition is a water-in-oil emulsion comprising a second flavorant and a colorant, the liquid center composition is completely surrounded by and is visible through the hard candy shell, wherein the liquid center composition has a contact angle of less than 80 degrees on a gelatin coated surface; wherein each unit of the plurality is individually unwrapped; and wherein the package comprises a moisture barrier over-wrap.

In an embodiment, a sugar-free liquid edible composition wherein the sugar-free liquid edible composition is a water-in-oil emulsion comprising i) a sugar polyol comprising xylitol, ii) glycerin, and iii) an emulsifier wherein the emulsifier is a glycerin based emulsifier, a polyglycerol based emulsifier, or a combination thereof; wherein the weight ratio of sugar polyol:glycerin is 1:1 to 4:1.

The above described and other features are exemplified by the following detailed description.

DETAILED DESCRIPTION

Disclosed herein are transparent or translucent liquid filled confectionery products, processes of making the confectionery products, and the confectionery products in loose, bulk packaged form. The confectionery has multiple phases, multiple components, and multiple textures. The confectionery comprises a liquid center composition where the liquid center composition is a water-in-oil emulsion, and a hard candy shell completely surrounding the liquid center composition. The hard candy shell is transparent or translucent, thereby allowing for the liquid center composition to be perceived upon visual inspection, specifically visible when viewed from any and all sides of the confectionery product piece, more specifically visible through all six sides of the hard candy shell.

The overall candy shape is non-limiting and can be of any three dimensional shape. In an embodiment, the shape is a three-dimensional shape that can be achieved by a deposit molding process, for example cube, cuboid (three dimensional rectangle), hemispherium, circular cone, circular truncated cone, three-sided pyramid, four-sided pyramid, a multi-sided pyramid (five, six, seven, eight, or more), and the like. In an embodiment, the product is cube-shaped.

In an embodiment, a confectionery product, specifically a cube-shaped confectionery product comprises a translucent hard candy shell comprising a first flavorant, and a liquid center composition wherein the liquid center composition is a water-in-oil emulsion comprising a second flavorant and a colorant, the liquid center composition is completely surrounded by and is visible through the hard candy shell; wherein the liquid center composition has a contact angle of less than 80 degrees on a gelatin coated surface.

In an embodiment, a package comprises a plurality of deposited confectionery products, specifically cube-shaped, deposited confectionery products, wherein each unit of the plurality is individually unwrapped, and wherein the package comprises a moisture barrier over-wrap.

Also disclosed herein is a sugar-free liquid edible composition wherein the sugar-free liquid edible composition is a water-in-oil emulsion. The sugar-free liquid edible composition can be used as a region in a confectionery product or medicament product such as a liquid center composition.

Confectionery Product Attributes

When consumed, the hard candy shell is first perceived followed by the liquid center composition after a side of the product (e.g. side of a cube) is breached due to dissolution in the consumer's mouth. In an embodiment, the liquid center composition is not tasted by the consumer until at least 20% of the hard candy shell is dissolved. The liquid center composition flavor and sensation is perceived for a long duration of time as an amount of liquid center composition remains adhered to the candy shell after shell breach and then is entirely consumed before the shell is entirely consumed.

Due to the use of the water-in-oil emulsion liquid center composition, there is a sharp flavor transition from a perception of the shell flavor to the perception of the liquid center composition flavor even if each region contains the same material (i.e. whether the same flavorant, same sensate, etc.).

In an embodiment, the confectionery, specifically the cube-shaped confectionery, provides a first flavor sensation when consumed that is entirely due to the first flavorant of the hard candy shell and a second flavor sensation later in time wherein the second flavor sensation is created by a combination of the first flavorant and the second flavorant of the liquid center composition.

In an embodiment, both the liquid center composition and the hard candy shell comprises menthol wherein the ratio of percent menthol in the liquid center composition to that in the hard candy shell is at least 1.5:1, specifically at least 1.75:1, more specifically at least 2:1, and yet more specifically at least 2.5:1 relative to the total weight of the confectionery piece.

The confectionery can provide breath freshening effect, freshness, an invigorating feeling, and a burst of flavor when the liquid center composition is released.

The flavor of the confectionery is long lasting, specifically lasting at least five minutes after consumption. Contributing to the long lasting flavor is that during consumption of the product, a portion of the liquid center material remains attached to the interior hard candy shell surface even after one minute after breach, such that at least 5% of the liquid center material remains, specifically at least 10%, and more specifically at least 20% of the liquid center material remains attached to the interior hard candy shell surface one minute after breach.

It has been found that the liquid center material having a contact angle of less than 80 degrees on a gelatin coated glass surface provides a good mouth coating feeling and spreads evenly in the oral cavity to give a long lasting liquid feeling and prolonged flavor release.

In an embodiment, the confectionery is generally cube-shaped, specifically a cube shape having rounded edges rather than sharp edges. The cube-shaped confectionery can have a dissolution surface area (DSA) of less than 45%, specifically less than 40%.

The confectionery is generally of small size yet with a high percent center fill content. In an embodiment, the confectionery piece is about 0.5 to about 6 grams (g), specifically about 1.0 to about 4 g, yet more specifically about 1.4 to about 2 g.

In an embodiment, the cube-shaped confectionery has a wall height of about 5 to about 20 millimeters (mm), specifically about 8 to about 17, more specifically, about 10 to about 15.

In an embodiment, the cube-shaped confectionery weighs less than 2 grams and has a distance between opposing walls of less than or equal to 0.5 inch (12.7 mm), and wherein five of six sidewalls are substantially straight and a sixth sidewall is arcuate.

In an embodiment, a confectionery product, specifically a cube-shaped confectionery product, prepared from an isomalt hard candy shell forms a microcrystallization layer on the surface of the product post forming. The microcrystallization layer can be formed by allowing the confectionery products to be conditioned at less than about 20 to about 25° C. with the low end of the range of about 0° C. and a relative humidity of less than about 45%, specifically less than about 40%, with the low end of the range being 0%. At these conditions, a transparent, non sticky product is formed which remains transparent and non sticky if stored unwrapped at conditions of <20-25° C. and <40-45% relative humidity. The hard candy shell can remain transparent or if conditioned at higher temperatures and relative humidity, becomes translucent. The microcrystallization layer can function as an anti-stick layer, allowing for the confectionery pieces to be packaged as loose, unwrapped units without sticking together in the package and to freely pour out of the package as individual units. As the individual pieces will not stick to one another there is no need to individually wrap each piece.

In an embodiment, the hard candy shell comprises an outer surface which permits free flow of a plurality of confectioneries from a container, wherein the individual units of the plurality have been in direct contact with each other for at least 30 days at STP (25° C., 77° F., 100 kPa, 14.504 psi, 0.986 atm) and 30% to 60% relative humidity.

The confectionery products comprising the water-in-oil emulsion liquid center composition exhibits high stability such that the product does not leak the liquid center composition through the shell after 8 weeks under accelerated aging conditions. Not wishing to be bound by theory but the stability can be due in part to the composition of the liquid center material as well as the method by which the products are formed. The water-in-oil emulsion does not appear to dissolve the hard candy shell as evidenced by x-ray tomography studies. Furthermore, as the confectionery is prepared by a co-depositing process, there are few to no points of weakness in the shell where the center-fill material can easily leak out of over time, unlike liquid center-fill hard candy products made using other processes such as rotary or chain die forming processes.

Specifically, the uniformity of the thickness of the shell walls formed by the co-deposit process helps to prevent the formation of thin shell wall regions, such as those found in rotary molded products. These thin regions of shell can potentially be dissolved by moisture, whether from the surroundings or within the confectionery product itself, thereby allowing the center-fill to leak from the product.

In an embodiment, less than 20% if the liquid center composition migrates into the hard candy shell during a 24 month shelf life.

In an embodiment, the confectionery exhibits less than a 15%, specifically less than a 10%, and more specifically less than a 5% reduction in an average hard candy shell thickness after aging for six weeks at 40° C. and 30-60% relative humidity.

In an embodiment, the liquid center composition is substantially free of voids having a cross sectional area greater than 0.5% of the cross sectional area of the confectionery after aging the confectionery for three weeks at 40° C. and 30-60% relative humidity.

Sugar-free Liquid Edible Composition/Liquid Center Composition

The sugar-free liquid edible composition, called "the liquid center composition" when used as a liquid center-fill in a hard candy shell, is a water-in-oil emulsion having a discontinuous aqueous phase dispersed in an oil phase. The water-in-oil emulsion comprises an edible oil, a sugar polyol, and optionally an emulsifier, along with other optional ingredients.

The sugar-free liquid edible composition is a liquid, specifically a liquid at 37° C. In an embodiment, the sugar-free liquid edible composition has a contact angle of less than 80 degrees on a gelatin coated surface. Such a property allows for the composition to provide the consumer with a good mouth-coating and liquid feeling as the composition spreads evenly in the oral cavity. The sugar-free liquid edible composition has a contact angle of less than 80 degrees on a gelatin coated surface, specifically about 0 to less than 80 degrees, more specifically about 10 to about 70 degrees, and yet more specifically about 20 to about 60 degrees.

The water-in-oil emulsion of the sugar-free liquid edible composition can comprise an edible oil for the hydrophobic phase. As used herein, the term "oil" refers to any lipid material and can be liquid at body temperature (about 37° C.) or less. Exemplary edible oil for use in the sugar-free liquid edible composition include fats and oils of vegetable origin, animal origin, or a combination thereof. Suitable vegetable fats can include oils from almond, canola, coconut, cocoa, cocoa butter, corn, cottonseed, grape seed, illipe, olive, palm, palm kernel, peanut, perilla, rapeseed, rice bran, safflower, sesame, shea, soybean, sunflower, or a combination thereof. The forgoing vegetable fats can be hydrogenated to varying degrees as desired or separated by fractional crystallization. Suitable animal fats include dairy fats such as milk fat and butter. Other exemplary lipid materials include triglycerides, fatty alcohols, fatty acids, or a combination thereof. The triglyceride is not limited although medium chain triglycerides, long chain triglycerides, and the like can be used, specifically medium chain triglycerides.

An edible oil can be present in the sugar-free liquid edible composition in an amount of about 5 to about 18 wt. % based on the total weight of the sugar-free liquid edible composition, specifically about 6 to about 16 wt. %, more specifically about 8 to about 15 wt. %, and yet more specifically about 10 to about 12 wt. %.

In an embodiment, the edible oil is a medium chain triglyceride. In an embodiment, the edible oil is a combination of a medium chain triglyceride and a hydrogenated vegetable oil.

The water-in-oil emulsion comprises a noncrystallized/non-solidified saccharide or sugar polyol as the discontinuous aqueous phase. The saccharide can include a monosaccharide, di-saccharide and poly-saccharide such as sucrose (sugar), dextrose, maltose, dextrin, xylose, ribose, glucose, mannose, galactose, fructose (levulose), lactose, invert sugar, fructo oligo saccharide, partially hydrolyzed starch, isomaltulose, high fructose corn syrup, polydextroses, or a combination thereof. The sugar polyol can be erythritol, galactitol, hydrogenated starch hydrolysate, isomalt, lactitol, maltitol, mannitol, polyglucitol, sorbitol, xylitol, or a combination thereof, wherein the sugar polyol can be in the form of a syrup. In an embodiment, the sugar polyol is maltitol, sorbitol, xylitol, or a combination thereof. In an embodiment, the sugar polyol comprises xylitol, noncrystallizing sorbitol syrup, maltitol syrup, or a combination thereof. In an embodiment, the sugar polyol is substantially free from crystallization such that there is less than about 10% crystalline sugar polyol in the water-in-oil emulsion.

In an embodiment, the sugar polyol can be isomalt, a disaccharide alcohol. Isomalt can be prepared by hydrogenating isomaltulose. Products of the hydrogenation can include 6-O-α-D-glucopyranosyl-D-sorbitol (1,6-GPS); 1-O-α-D-glucopyranosyl-D-sorbitol (1,1-GPS); 1-O-α-D-glucopyranosyl-D-mannitol (1,1-GPM); 6-O-α-D-glucopyranosyl-D-mannitol (1,6-GPM); and mixtures thereof. Some commercially available isomalt materials include an almost equimolar mixture of 1,6-GPS, and 1,1-GPM. Other isomalt materials can include pure 1,6-GPS; 1,1-GPS; 1,6-GP; and 1,1-GPM. Still other isomalt materials can include mixtures of 1,6-GPS; 1,1-GPS; 1,6-GPM; and 1,1-GPM at any ratio.

A sugar polyol can be present in the sugar-free liquid edible/composition in an amount of about 40 to about 65 wt. % based on the total weight of the sugar-free liquid edible composition, specifically about 43 to about 60 wt. %, more specifically about 46 to about 57 wt. %, and yet more specifically about 48 to about 52 wt. %.

The sugar-free liquid edible composition can further comprise an emulsifier. Suitable emulsifiers for use in the sugar-free liquid edible composition can have a low HLB value useful in the continuous lipophilic phase for preparing water-in-oil emulsions. An exemplary HLB value for water-in-oil emulsions can be in the range of about 1 to about 10, specifically about 4 to about 6. The emulsifier of the sugar-free liquid edible composition can be a glycerin based emulsifier, a polyglycerol based emulsifier, or a combination thereof. Exemplary emulsifiers include a monoglycerol fatty acid ester, lecithin, an organic acid glycerin fatty acid ester, a polyglycerol fatty acid ester, a polyglycerol condensed ricinoleic acid ester, a sorbitan fatty acid ester, a sucrose fatty acid ester, a propylene glycol fatty acid ester, or a combination thereof. Specific emulsifiers include condensed triglycerin ricinoleate, condensed tetraglycerin ricinoleate, condensed hexaglycerin ricinoleate, condensed pentaglycerin ricinoleate, monoglyceride citrate, pentaglycerin trioleate, decaglycerin pentaoleate, decaglycerin decaoleate, pentaglycerin trioleate, or a combination thereof. In an embodiment, the emulsifier is lecithin, specifically high purity lecithin. In another embodiment, the emulsifier is a combination of a sucrose fatty acid ester and lecithin, specifically high purity lecithin.

The emulsifier can be present in the sugar-free liquid edible composition in an amount of about 1.0 to about 5.0 wt. % based on the total weight of the sugar-free liquid edible composition, specifically about 1.5 to about 4.5 wt. %, more specifically about 2.5 to about 4.0 wt. %, and yet more specifically about 3.0 to about 3.5 wt. %.

The sugar-free liquid edible composition optionally further comprises a flavorant, a colorant, a sensate or a combination thereof as described herein; specifically, the sugar-free liquid edible composition comprises a colorant and a cooling agent; more specifically the sugar-free liquid edible composition comprises a flavorant, a colorant, and a cooling agent wherein the cooling agent is menthol; yet more specifically the sugar-free liquid edible composition comprises a flavorant, a colorant, a cooling agent, a food acid or salt thereof, and a high intensity sweetener as disclosed herein. In an embodiment, the food acid or salt thereof can be citric, lactic, malic, a salt thereof, or a combination thereof.

The amount and type of flavorant used in the sugar-free liquid edible composition can be chosen based on the targeted release profile and flavor intensity desired. The flavorant can be present in the sugar-free liquid edible composition in an amount of about 0.001 to about 4 wt. % based on the total weight of the sugar-free liquid edible composition, specifically about 0.01 to about 3 wt. %, more specifically about 0.1 to about 2 wt. %, and yet more specifically about 0.5 to about 1 wt. %.

The sensate, specifically a cooling agent, can be present in the sugar-free liquid edible composition in an amount of about 0.01 to about 4 wt. % based on the total weight of the sugar-free liquid edible composition, specifically about 0.1 to about 3 wt. %, more specifically about 0.5 to about 2 wt. %, and yet more specifically about 1 to about 1.5 wt. %.

The high intensity sweetener can be present in the sugar-free liquid edible composition in an amount of about 0.001 to about 2 wt. % based on the total weight of the sugar-free liquid edible composition, specifically about 0.01 to about 1.5 wt. %, more specifically about 0.1 to about 1 wt. %, and yet more specifically about 0.3 to about 0.8 wt. %.

The sugar-free liquid edible composition may further comprise a non-aqueous polar liquid such as glycerin, propylene glycol, polyethylene glycol (e.g. PEG-200, PEG-300, PEG-400, and PEG-600), or a combination thereof. In an embodiment, the sugar-free liquid edible composition comprises glycerin.

The non-aqueous polar liquid can be present in the sugar-free liquid edible composition in an amount of about 15 to about 40 wt. % based on the total weight of the sugar-free liquid edible composition, specifically about 17 to about 37 wt. %, more specifically about 20 to about 33 wt. %, and yet more specifically about 23 to about 30 wt. %.

In an embodiment, the sugar-free liquid edible composition is a water-in-oil emulsion comprising a sugar polyol and glycerin having a weight ratio of 1:1 to 4:1 sugar polyol:glycerin, specifically 1.5:1 to 3:1, and more specifically 2:1 to 2.5:1.

In an embodiment, the sugar-free liquid edible composition is a water-in-oil emulsion comprising a sugar polyol comprising xylitol, lecithin, and glycerin having a weight ratio of 1:1 to 4:1 sugar polyol:glycerin.

In an embodiment, the sugar-free edible composition is a water-in-oil emulsion comprising a sugar polyol comprising xylitol, lecithin, a medium chain triglyceride, glycerin, optionally a hydrogenated vegetable oil, and a moisture content of about 0.01 to about 4.0 wt. % based on the total weight of the edible composition.

The sugar-free liquid edible composition can further optionally comprise a functional ingredient, particulates such as fruit pieces, or a combination thereof, as disclosed herein.

In an embodiment, the amount of moisture present in the sugar-free liquid edible composition is about 0.01 to about 4.0 wt. % based on the total weight of the sugar-free liquid edible composition, specifically about 0.1 to about 3.5 wt. %, more specifically about 1.0 to about 3.0 wt. %, and yet more specifically about 1.5 to about 2.5 wt % based on the total weight of the sugar-free liquid edible composition.

The sugar-free liquid edible composition can be used as a liquid center composition in the confectionery products. An amount of liquid center composition to the total confectionery weight can be about 5 to about 70 wt. %, specifically about 10 to about 60 wt. %, more specifically about 15 to about 50 wt. %, still more specifically about 20 to about 40 wt. %, and still yet more specifically about 25 to about 30 wt. % based on the total confectionery product weight.

The sugar-free liquid edible composition can be used as a region in a confectionery product or medicament product. In an embodiment, the confectionery product or medicament product comprises a first region comprising the sugar-free liquid edible composition and a second region at least partially surrounding the first region. The second region can be prepared from another confectionery composition. The confectionery product or medicament product can be a candy, chewing gum, pastille, troche, lozenge, or tablet. The medicament product can further comprise an active pharmaceutical agent in the first region, the second region or both.

The sugar-free liquid edible composition can generally be prepared by separately forming a sugar polyol phase and an oil phase and then combining under conditions to form a water-in-oil emulsion.

The sugar polyol phase can be prepared by heating the sugar polyol to form a molten mass (e.g. about 130 to about 160° C.). If used, the non-aqueous polar liquid is added to the molten mass. The molten mass is cooled (e.g. to about 45 to about 70° C.) and the colorant, flavorant, and sensate are added along with any optional hydrophilic ingredients to form a final sugar polyol phase.

The oil phase can generally be prepared by heating an edible oil to up to about 80° C., adding an emulsifier, if used. Other optional hydrophobic ingredients can be added to form a final oil phase which is combined with the final sugar polyol phase with mixing to form a water-in-oil emulsion.

Hard Candy Shell

The hard candy shell of the confectionery is a hard, essentially amorphous (glassy) sugar polyol material that is transparent or translucent, specifically transparent to allow the liquid center composition to be visible through the shell. The hard candy shell completely surrounds the liquid center composition. The hard candy shell generally comprises a cooked saccharide or cooked sugar polyol, or a combination thereof. The saccharide and sugar polyol can be in dry form or in syrup/solution form prior to cooking, or a blend of dry and syrup/solution forms.

The saccharide can be a mono-saccharide, di-saccharide and poly-saccharide such as sucrose (sugar), dextrose, maltose, dextrin, xylose, ribose, glucose, mannose, galactose, fructose (levulose), lactose, invert sugar, fructo oligo saccharide, partially hydrolyzed starch, isomaltulose, high fructose corn syrup, polydextroses, or a combination thereof.

The sugar polyol can be erythritol, galactitol, hydrogenated starch hydrolysate, isomalt, lactitol, maltitol, mannitol, polyglucitol, sorbitol, xylitol, or a combination thereof. In an embodiment, the sugar polyol is maltitol, sorbitol, xylitol, or a combination thereof. In an embodiment, the sugar polyol of the hard candy shell can be isomalt, maltitol, or a combination thereof, specifically isomalt.

The hard candy shell can comprise the saccharide or sugar polyol in an amount of about 90 to about 100 wt. % based on the total weight of the hard candy shell, specifically about 92 to about 98 wt. %, and yet more specifically about 94 to about 96 wt. %.

The hard candy shell can further comprise a flavorant, a food acid or salt thereof, a sensate, a high intensity sweetener, or a combination thereof.

The amount and type of flavorant used in the hard candy shell can be chosen based on the targeted release profile and flavor intensity desired. The flavorant can be present in the hard candy shell in an amount of about 0.001 to about 1.5 wt. % based on the total weight of the hard candy shell, specifically about 0.01 to about 1 wt. %, and yet more specifically about 0.1 to about 0.6 wt. %.

The sensate, specifically the cooling agent, can be present in the hard candy shell in an amount of about 0.001 to about 1 wt. % based on the total weight of the hard candy shell, specifically about 0.01 to about 0.7 wt. %, and yet more specifically about 0.1 to about 0.5 wt. %.

The high intensity sweetener can be present in the hard candy shell in an amount of about 0.001 to about 1 wt. % based on the total weight of the hard candy shell, specifically about 0.01 to about 0.7 wt. %, and yet more specifically about 0.1 to about 0.5 wt. %.

The optional food acid can be present in the hard candy shell in an amount of about 0.001 to about 1.5 wt. % based on the total weight of the hard candy shell, specifically about 0.01 to about 1 wt. %, and yet more specifically about 0.1 to about 0.8 wt. %.

The hard candy shell may optionally further comprise a functional ingredient, a colorant as long as the center-fill can be seen through the shell, or a combination thereof.

The hard candy shell of the confectionery does not break up as it is being consumed, rather it dissolves slowly in the consumer's mouth.

The hard candy shell can be prepared by cooking a sugar polyol and optional water to about 140 to about 170° C. optionally under vacuum conditions to form a molten mass (also referred to as "hard candy shell melt") having less than about 3% moisture. Prior to the addition of the additional ingredients, the molten mass can be cooled slightly. Additional ingredients such as flavorant, a sensate, a food acid or a salt thereof, a high intensity sweetener, or a combination thereof are then added to the molten mass with mixing to form the final hard candy shell melt that is then molded into a confectionery product.

The moisture content of the hard candy shell melt can be about 0.1 to about 3 wt. % based on the total weight of the hard candy shell melt, specifically about 0.5 to about 2 wt. %, and yet more specifically about 1 to about 1.5 wt. %.

Methods known in the art of making hard boiled confectioneries include those utilizing fire cookers, vacuum cookers, and scraped-surface cookers (aka high speed atmospheric cookers).

In a suitable example of a method utilizing fire cookers, the desired quantity of the sugar polyol is dissolved in water by heating in a kettle until dissolved. Additional optional sugar polyols can be added and cooking continued until a final temperature of about 145-165° C. is achieved. The mix is then cooled, worked as a plastic-like mass, and admixed optional additional ingredients such as flavors, colorants, high-intensity sweeteners, and the like.

A suitable example of a method utilizing vacuum cookers, the sugar polyol components are boiled at a temperature of about 125-132° C., vacuum is applied and additional water is boiled off without extra heating. When cooking is complete, the mass is a semi-solid having a plastic-like consistency. Optional additional ingredients are admixed into the mass at this point by conventional methods.

In a suitable example of a method using scraped-surface cookers, a film of a mixture of the sugar polyol components is spread on a heat exchange surface and heated to about 165-170° C. within a few minutes. The composition is then rapidly cooled to about 100-120° C. and worked as a plastic-like mass, mixing in any optional additional ingredients.

In the foregoing methods, the cooking temperature should be sufficiently high to drive water from the mix. Where vacuum is employed, lower temperatures can typically be used. In the foregoing methods, the additional ingredients are specifically mixed for a time effective to provide a uniform distribution of the materials, for example about 4 to about 10 minutes.

In an embodiment, a confectionery product, specifically a cube-shaped confectionery product, comprises a translucent hard candy shell comprising a first flavorant, and a liquid center composition wherein the liquid center composition is a water-in-oil emulsion comprising a sugar polyol comprising xylitol, lecithin, a medium chain triglyceride and optionally a hydrogenated vegetable oil, glycerin, a second flavorant, a colorant and a moisture content of about 0.01 to about 4.0 wt. % based on the total weight of the liquid center composition, the weight ratio of sugar polyol:glycerin is 1:1 to 4:1; wherein the liquid center composition has a contact angle of less than 80 degrees on a gelatin coated surface; and wherein the liquid center composition is completely surrounded by and is visible through the hard candy shell.

Confectionery Ingredients: Flavorant

The sugar-free liquid edible composition, hard candy shell, or both can comprise a flavorant. More than one flavorant can be used in either the shell or center and the flavorant of the shell can be different or the same as the flavorant in the sugar-free liquid edible composition. Exemplary flavorants (flavor, flavoring agent) that can be used include those artificial or natural flavors known in the art, for example synthetic flavor oils, natural flavoring aromatics and/or oils, oleoresins, extracts derived from plants, leaves, flowers, fruits, and the like, or a combination thereof. Non-limiting representative flavors include oils such as spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, cassia oil, and citrus oils including lemon, orange, lime, grapefruit, vanilla, fruit essences/flavors, including apple, pear, peach, grape, strawberry, raspberry, blackberry, cherry, plum, pineapple, apricot, banana, melon, tropical fruit, mango, mangosteen, pomegranate, papaya, honey lemon, and the like, or a combination thereof.

Other types of flavorants include various aldehydes and esters such as cinnamyl acetate, cinnamaldehyde, citral diethylacetal, dihydrocarvyl acetate, eugenyl formate, p-methylamisol, acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin).

Sensate

The sugar-free liquid edible composition, hard candy shell, or both can further comprise a sensate. More than one sensate can be used in either the shell or center and the sensate of the shell can be different or the same as the sensate in the sugar-free liquid edible composition. Exemplary sensates include cooling agents, warming agents, tingling agents, effervescent agents, or a combination thereof. Cooling agents are additives that provide a cooling or refreshing effect in the mouth, in the nasal cavity, or on skin. For example, among the useful cooling agents are included menthol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-2,2-diisopropylbutanamide, N-ethyl-p-menthane-3-carboxamide (WS-3), ethyl ester of N-[[5-methyl-2-(1-methylethyl)cyclohexyl]carbonyl]glycine (WS-5), as well as the substantially pure ethyl ester of N-[[5-methyl-2-(1-methylethyl)cyclohexyl]carbonyl]glycine as disclosed in U.S. Pat. No. 7,189,760 to Erman, et al which is incorporated in its entirety herein by reference, isopulegol, menthyloxy propane diol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, N-(4-cyanomethylphenyl) p-menthanecarboxamide (G-180), Japanese mint oil, peppermint oil, 3-(1-menthoxy) ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Haarman & Reimer, FEMA 3748, tradename FRESCOLAT® type ML), WS-30, WS-14, Eucalyptus extract (p-Mehtha-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; Menthol methyl ether, menthyl pyrrolidone carboxylate; 2,5-dimethyl-4-(1-pyrrolidinyl)-3(2H)-furanone; cyclic α-keto enamines, cyclotene derivatives such as cyclopentenes including 3-methyl-2-(1-pyrrolidinyl)-2-cyclopenten-1-one and 5-methyl-2-(1-pyrrolidinyl)-2-cyclopenten-1-one, compounds of the formula:

wherein B is selected from H, CH₃, C₂H₅, OCH₃, OC₂H₅; and OH; and wherein A is a moiety of the formula-CO-D, wherein D is selected from the following moieties: (i) —NR¹R², wherein R¹ and R² are independently selected from H and C₁-C₈ straight or branched-chain aliphatic, alkoxyalkyl, hydroxyalkyl, araliphatic and cycloalkyl groups, or R¹ and R² together with the nitrogen atom to which they are attached form part of an optionally-substituted, five- or six-membered heterocyclic ring; (ii) —NHCH₂COOCH₂CH₃, —NHCH₂CONH₂, —NHCH₂CH₂OCH₃, —NHCH₂CH₂OH, —NHCH₂CH(OH)CH₂OH and (iii) a moiety selected from the group consisting of:

as disclosed in PCT Patent Application WO2006/125334 to Bell et al. which is incorporated in its entirety herein by reference, among others; or a combination thereof. Other compounds include the alpha-keto enamines disclosed in U.S. Pat. No. 6,592,884 to Hofmann et al. which is incorporated in its entirety herein by reference. These and other suitable cooling agents are further described in the following U.S. patents, all of which are incorporated in their entirety by reference hereto: U.S. Pat. Nos. 4,230,688; 4,032,661; 4,459,425; 4,178,459; 4,296,255; 4,136,163; 5,009,893; 5,266,592; 5,698,181; 6,277,385; 6,627,233; 7,030,273. Still other suitable cooling agents are further described in the following U.S. Published Patent Applications, all of which are incorporated in their entirety by reference hereto: U.S. 2005/0222256; 2005/0265930.

Warming agents can be selected from a wide variety of compounds known to provide the sensory signal of warming to the user. These compounds offer the perceived sensation of warmth, particularly in the oral cavity, and often enhance the perception of flavors, sweeteners and other organoleptic components. Among the useful warming agents included are vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamylether, vanillyl alcohol n-hexylether, vanillyl alcohol methylether, vanillyl alcohol ethylether, gingerol, shogaol, paradol, zingerone, capsaicin, dihydrocapsaicin, nordihydrocapsaicin, homocapsaicin, homodihydrocapsaicin, ethanol, isopropol alcohol, iso-amylalcohol, benzyl alcohol, glycerine, or a combination thereof.

In an embodiment, tingling agents may be employed to provide a tingling, stinging or numbing sensation to the user. Tingling agents include, but are not limited to: Jambu Oleoresin or para cress (*Spilanthes* sp.), in which the active ingredient is Spilanthol; Japanese pepper extract (*Zanthoxylum peperitum*), including the ingredients known as Saanshool-I, Saanshool-II and Sanshoamide; perillartine; 4-(1-menthoxymethyl)-2-phenyl-1,3-dioxolane; black pepper extract (*piper nigrum*), including the active ingredients chavicine and piperine; Echinacea extract; Northern Prickly Ash extract; trans-pellitorin, and red pepper oleoresin; or a combination thereof. In an embodiment, alkylamides extracted from materials such as jambu or sanshool may be included.

High Intensity Sweetener

The sugar-free liquid edible composition, hard candy shell, or both may comprise a high intensity sweetener. More than one high intensity sweetener can be used in either the shell or center and the high intensity sweetener of the shell can be different or the same as the high intensity sweetener in the sugar-free liquid edible composition. A "high intensity sweetener" as used herein means agents having a sweetness greater than the sweetness of sucrose. In an embodiment, a high intensity sweetener has a sweetness that is at least 100 times that of sugar (sucrose) on a per weight basis, specifically at least 500 times that of sugar on a per weight basis. In an embodiment the high intensity sweetener is at least 1,000 times that of sugar on a per weight basis, more specifically at least 5,000 times that of sugar on a per weight basis. The high intensity sweetener can be selected from a wide range of materials, including water-soluble sweeteners, water-soluble artificial sweeteners, water-soluble sweeteners derived from naturally occurring water-soluble sweeteners, dipeptide based sweeteners, and protein based sweeteners. Combinations comprising one or more sweeteners or one or more of the foregoing types of sweeteners can be used. Without being limited to particular sweeteners, representative categories and examples include:

water-soluble sweetening agents such as dihydrochalcones, monellin, steviosides, rebaudiosides, glycyrrhizin, dihydroflavenol, monatin, and L-aminodicarboxylic acid aminoalkenoic acid ester amides, such as those disclosed in U.S. Pat. No. 4,619,834, or a combination thereof;

water-soluble artificial sweeteners such as soluble saccharin salts, i.e., sodium or calcium saccharin salts, cyclamate salts, acesulfame salts, such as the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, or a combination thereof;

dipeptide based sweeteners, for example the L-aspartic acid derived sweeteners such as L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenyl-alanine; L-aspartyl-L-(1-cyclohexen)-alanine, neotame, or a combination thereof;

water-soluble sweeteners derived from naturally occurring water-soluble sweeteners, such as steviosides and stevia derived compounds such as but not limited to steviol glycosides such as rebaudiocides including rebaudiocide A, and the like, lo han quo and lo han quo derived compounds such as iso-mogroside V and the like, chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-furanoside, or 4,1'-dichloro-4,1'-dideoxygalactosucrose; 1',6'-dichloro1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro4,6,1',6'-tetradeoxygalacto-sucrose; 4,6,1',6'-tetradeoxy-sucrose, or a combination thereof;

protein based sweeteners such as thaumaoccous danielli, talin, or a combination thereof; and amino acid based sweeteners.

Colorant

The sugar-free liquid edible composition can further comprise a colorant. Coloring agents (colors, colorants, colorings) can be used in amounts effective to produce a desired color for the composition which can be perceived visually through the hard candy shell, for example. Suitable coloring agents include pigments, natural food colors and dyes suitable for food, drug, and cosmetic applications. Suitable colors include annatto extract (E160b), bixin, norbixin, astaxanthin, dehydrated beets (beet powder), beetroot red/betanin (E162), ultramarine blue, canthaxanthin (E161g), cryptoxanthin (E161c), rubixanthin (E161d), violanxanthin (E161e), rhodoxanthin (E161f), caramel (E150 (a-d)), β-apo-8'-carotenal (E160e), β-carotene (E160a), alpha carotene, gamma carotene, ethyl ester of beta-apo-8 carotenal (E160f), flavoxanthin (E161a), lutein (E161b), cochineal extract (E120), carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haematococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminium (E173), silver (E174), gold (E175), pigment rubine/lithol rubine BK (E180), calcium carbonate (E170), carbon black (E153), black PN/brilliant black BN (E151), green S/acid brilliant green BS (E142), or a combination thereof. In an embodiment, certified colors can include FD&C aluminum lakes, or a combination thereof. A full recitation of all FD& C colorants and their corresponding chemical structures may be found in the Kirk-Othmer Encyclopedia of Chemical Technology, 4th Edition, in volume 1 at pages 492-494, which text is incorporated herein by reference.

Coloring agents can also include food grade glitter or food grade pearlescent pigments. The edible glitter can include a food grade colorant and a carrier such as a sugar, a sugar alcohol, a saccharide, a disaccharide, a polysaccharide, a hydrocolloid material, or a combination thereof. Exemplary glitter includes the commercially available Edible Glitter™ from Watson Inc. of West Haven, Conn. The coloring agent can include food grade pearlescent pigments prepared from mica optionally coated with titanium dioxide, iron oxide, and the like.

The hard candy shell can optionally further comprise a colorant as long as the liquid center composition can be visually perceived through the hard candy shell. In an embodiment, the hard candy shell comprises glitter or other speckles. In an embodiment, the hard-candy shell may be transparent, translucent, or clear-and-colorless; however, the hard candy shell may contain a colorant as far as its transparency can be maintained to allow the sugar-free liquid edible center therein visible from the outside.

Food Acid or Salt Thereof

The sugar-free liquid edible composition, hard candy shell, or both may comprise a food acid or salt thereof. More than one food acid or salt thereof can be used in either the shell or center and the food acid or salt thereof of the shell can be different or the same as the food acid or salt thereof in the sugar-free liquid edible composition. The food acid can be in free or buffered form. Exemplary food acids and food acid salts include acetic acid, adipic acid, ascorbic acid, butyric acid, citric acid, formic acid, fumaric acid, glyconic acid, lactic acid, phosphoric acid, malic acid, oxalic acid, succinic acid, tartaric acid, and alkali metal salts thereof (e.g., sodium citrate dihydrate), or a combination thereof.

Functional Ingredients

Exemplary functional ingredients for use in the sugar-free liquid edible composition, hard candy shell, or both include a breath freshener, a dental care component, an active, an herbal, an effervescing system, an appetite suppressor, a vitamin, a micronutrient, a mouth moistening component, a throat care component, an energy boosting agent, a concentration boosting agent, or a combination thereof.

Process to Prepare the Confectionery Product

The confectionery can be prepared by co-depositing the hard candy shell melt and the liquid center composition into a mold. Specifically, the forming process can be performed by first depositing the hard candy shell melt for a first period of time followed by simultaneously depositing the liquid center composition and the hard candy shell melt for a second period of time and then depositing the hard candy shell melt for a third period of time, and then allowing the components to cool to form the confectionery product.

The co-depositing can be achieved, for example, by using a depositor having a double pipe structure comprising an inner pipe and an outer pipe provided on an outer side of the inner pipe with a gap. The liquid center composition is deposited from the inner pipe and the hard candy shell melt from the gap. The deposited product is then cooled and de-molded. The co-depositing process includes the process described in WO2011010723, incorporated herein by reference.

The temperature of the liquid center composition during co-depositing is about 50 to about 70° C., specifically about 60° C. The temperature of the hard candy shell melt during co-depositing is about 125 to about 155° C., specifically about 140° C.

The co-depositing process provides precision in locating the center-fill within the confectionery piece which is substantially centered within a symmetrical shell. The shape of the center-fill portion can be substantially rounded or spherical. The co-depositing process also provides a shell with minimized bubble formation thereby providing a hard candy shell having a very smooth outer surface as well as a smooth feeling when dissolved in the consumer's mouth as bubbles are known for forming sharp edges in a hard boiled candy product. The co-depositing process also allows for the formation of confectionery having a high ratio of center-fill to shell.

In an embodiment, the liquid center material is positioned within the hard candy shell such that a distance between any point on a periphery of the liquid center and the nearest point on an outer wall of the hard candy shell is greater than 0.6 mm and there is no void in the path connecting the points that is greater than 20% of the distance.

Packaged Confectionery Product

A plurality of confectionery products, specifically cube-shaped confectionery products, can be packaged as unwrapped, loose units in a container or bag. Exemplary packaging includes cartons, boxes, cylindrical containers made of paper, plastic, and the like. In an embodiment, the package comprises a moisture barrier or has a moisture barrier overwrap.

The features and advantages are more fully shown by the following examples which are provided for purposes of illustration, and are not to be construed as limiting the invention in any way.

EXAMPLES

Example 1

Cube-shaped confectionery products are prepared from shell formulations set out in Table 1. And liquid center compositions set out in Table 2.

TABLE 1

| | Shell | | | | | |
|---|---|---|---|---|---|---|
| Ingredient | Mint 1 | Fruit 1 | Mint 2 | Fruit 2 | Mint 3 | Fruit 3 |
| Cooked sugar polyol | | | | | | |
| Maltitol | 98.5-99.8 | 98.5-99.8 | — | — | 49.25-49.8 | 49.25-49.8 |
| Isomalt | — | — | 98.5-99.8 | 98.5-99.8 | 49.25-49.8 | 49.25-49.8 |
| Ace K and/or sucralose | 0-0.1 | 0-0.1 | 0-0.1 | 0-0.1 | 0-0.1 | 0-0.1 |
| Food acid | — | 0.01-1.2 | — | 0.01-1.2 | — | 0.01-1.2 |
| Water | 0.05-0.3 | 0.05-0.3 | 0.05-0.3 | 0.05-0.3 | 0.05-0.3 | 0.05-0.3 |
| Menthol | 0.1-0.2 | 0.1-0.2 | 0.1-0.2 | 0.1-0.2 | 0.1-0.2 | 0.1-0.2 |
| Cooling agent | 0.01-0.2 | 0-0.1 | 0.01-0.2 | 0-0.1 | 0.01-0.2 | 0-0.1 |
| Mint flavor | 0.01-0.4 | — | 0.01-0.4 | — | 0.01-0.4 | — |
| Fruit flavor | — | 0.01-0.4 | — | 0.01-0.4 | — | 0.01-0.4 |
| Total | 100 | 100 | 100 | 100 | 100 | 100 |

The shell is generally prepared by cooking a mixture of sugar polyol and water at about 155° C., optionally under vacuum to achieve a moisture content at or below 3 wt. %. The cooked mixture is cooled slightly and flavorant, food acid, high intensity sweetener, and/or sensate are added to the cooled mixture to form a shell melt which is maintained as a melt for the co-depositing process.

TABLE 2 a: Liquid center composition

| Ingredient | Mint 1 | Fruit 1 | Mint 2 | Fruit 2 | Mint 3 | Fruit 3 |
|---|---|---|---|---|---|---|
| Maltitol | 5-8 | 5-8 | 6-7 | 6-7 | 0-5 | 0-5 |
| Xylitol | 17-21 | 17-21 | 17-21 | 17-21 | 17-21 | 17-21 |
| Sorbitol | 20-27 | 20-27 | 20-26 | 20-26 | 20-32 | 20-32 |
| Glycerin | 32-35 | 32-35 | 32-35 | 32-35 | 32-35 | 32-35 |
| Colorant | 0.025-0.9 | 0.025-0.9 | 0.025-0.9 | 0.025-0.9 | 0.025-0.9 | 0.025-0.9 |
| Water | 0.05-0.35 | 0.05-0.35 | 0.05-0.35 | 0.05-0.35 | 0.05-0.35 | 0.05-0.35 |
| Menthol | 0.7-2.5 | 0.7-2.5 | 0.7-2.5 | 0.7-2.5 | 0.7-2.5 | 0.7-2.5 |
| Lecithin | 2.3-2.6 | 2.3-2.6 | 2.3-2.6 | 2.3-2.6 | 2.3-2.6 | 2.3-2.6 |
| Medium Chain Triglycerides | 11-12 | 11-12 | 11-12 | 11-12 | 11-12 | 11-12 |
| Ace K | 0-0.06 | 0-0.06 | 0-0.06 | 0-0.06 | 0-0.06 | 0-0.06 |
| Cooling agent | 0.01-0.15 | 0.01-0.15 | 0.01-0.15 | 0.01-0.15 | 0.01-0.15 | 0.01-0.15 |
| Mint or other non-fruit flavor | 0.01-1.8 | — | 0.01-1.8 | — | 0.01-1.8 | — |
| Fruit flavor | — | 0.01-0.08 | — | 0.01-0.08 | — | 0.01-0.08 |
| Total | 100 | 100 | 100 | 100 | 100 | 100 | b: Liquid center composition

| Ingredient | Mint 4 | Fruit 4 | Mint 5 | Fruit 5 |
|---|---|---|---|---|
| Maltitol | 6-9 | 6-9 | 6-9 | 6-9 |
| Xylitol | 19-25 | 19-25 | 20-25 | 20-25 |
| Sorbitol | 24-30 | 24-30 | 24-30 | 24-30 |
| Glycerin | 22-27 | 22-27 | 22-26 | 22-26 |
| Colorant | 0.025-0.9 | 0.025-0.9 | 0.025-0.9 | 0.025-0.9 |
| Water | 0.05-0.3 | 0.05-0.3 | 2.0-3.2 | 2.0-3.2 |
| Menthol | 0.7-2.5 | 0.7-2.5 | 0.7-2.5 | 0.7-2.5 |
| Lecithin | 2.2-2.6 | 2.2-2.6 | 2.2-2.6 | 2.2-2.6 |
| Medium Chain Triglycerides | 6.0-10 | 6.0-10 | 10-12 | 10-12 |
| Hydrogenated vegetable oil | 2.0-4.0 | 2.0-4.0 | — | — |
| DK Ester ® sucrose fatty acid esters F-90, HLB 9.5 available from Dai-Ichi Kogyo Seiyaku Co., Ltd. of Japan | — | — | 0.5-2.0 | 0.5-2.0 |
| Ace K | 0-0.06 | 0-0.06 | 0-0.06 | 0-0.06 |
| Cooling agent | 0.01-0.15 | 0.01-0.15 | 0.01-0.15 | 0.01-0.15 |
| Mint or other non-fruit flavor | 0.01-1.8 | — | 0.01-1.8 | — |
| Fruit flavor | — | 0.01-0.08 | — | 0.01-0.08 |
| Total | 100 | 100 | 100 | 100 |
| Moisture content of liquid center | 0.05-0.35 | 0.05-0.35 | 2.0-3.2 | 2.0-3.2 |

The liquid center composition is generally prepared by combining maltitol, xylitol, and/or sorbitol with heating followed by the addition of glycerin, colorant, water, high intensity sweetener, and flavorant to form a hydrophilic phase. In a separate container medium chain triglycerides and/or hydrogenated vegetable oil, and lecithin are mixed to form an oil phase. In the process to prepare liquid center Mint 5 and Fruit 5, water is combined with the polyols before cooking the polyols with the sucrose fatty acid esters. The hydrophilic phase and the oil phase are combined with rapid stirring to form a water-in-oil emulsion.

The confectionery composition is generally prepared by a co-depositing process where the temperature of the liquid center composition during depositing is about 60° C. and the temperature of the hard candy shell melt during co-depositing is about 140° C. The wt. ratio of center to shell is 15-20:85-80.

Example 2

Wettability Study

A liquid center composition was studied to determine its mouth coating effects. When there is good wetting of a surface with a liquid, the liquid spreads over the surface of the material to form a thin film. The degree of wettability can be measured using contact angle (θ), the angle formed between a surface and a drop of liquid material sitting on the surface. The smaller the contact angle (θ), the greater the tendency for the liquid to spread over the surface, and the more the surface is wetted by the liquid. If the contact angle is less than 90 degrees the liquid is said to wet the surface; if it is greater than 90 degrees it is said to be non-wetting; while a zero contact angle represents complete wetting of the surface.

In this study, gelatin-coated glass cover slips are used as a model of the human oral mucosal membrane. The lower the contact angle on the surface of the gelatin-coated cover-slip, the better the liquid is wetting the surface, and likewise the better it is able to wet the oral mucosa.

Glass cover slips were dipped in a hot 20% gelatin solution and left to dry. The gelatin-coated slide can be considered an aqueous phase (solution), so that the water-in-oil emulsion interacts with the surface.

An Attension Theta optical tensiometer is used to measure the contact angle formed by a drop of liquid on the surface of the gelatin-coated slip.

The sample of liquid center material was brought to room temperature prior to measurement. A small amount of the liquid sample was drawn into a micro liter syringe. The syringe was then mounted into the proper place above the stage. The gelatin coated cover slip was centered on the stage and the camera was focused. One drop of approximately 10 micro liters was dropped onto slide and the measurement was taken.

The liquid center composition formulation studied contains the ingredients outlined in Table 3. below.

TABLE 3

| Ingredient | Amount (wt. %) |
| --- | --- |
| Powder Maltitol | 6.6 |
| Xylitol | 19.6 |
| Powder Sorbitol | 23.5 |
| Glycerin | 33.2 |
| Colorant | 0.1 |
| Potable Water | 0.4 |
| Flavorant (mint) | 2.7 |
| Lecithin | 2.6 |
| Medium Chain Triglycerides | 11.3 |
| Total | 100 |

The liquid center composition is prepared by combining maltitol, xylitol, and sorbitol with heating followed by the addition of glycerin, colorant, water, and flavorant to form a hydrophilic phase. In a separate container medium chain triglycerides and lecithin are mixed to form an oil phase. The hydrophilic phase and the oil phase are combined with rapid stirring to form a water-in-oil emulsion.

A comparative conventional aqueous center-fill formulation was prepared and measured for contact angle using the same procedure previously discussed. The Comparative center-fill contained 95 wt. % high fructose corn syrup, 5 wt. % sugar, and 15 wt. % glycerin.

The results of the study of ten measurements for the liquid center composition and five for the Comparative center-fill are found in Table 4 below.

TABLE 4

| Sample | Contact Angle (degrees) | | | |
| --- | --- | --- | --- | --- |
| | Mean Left | Mean Right | Standard Deviation Left | Standard Deviation Right |
| Liquid center composition | 57.68 | 57.61 | 9.38 | 8.47 |
| Comparative center-fill | 104.442 | 104.322 | 9.83 | 9.61 |

As the results show, the contact angle for the liquid center composition that is a water-in-oil emulsion is much lower than for the Comparative center-fill formulation. The liquid center composition interacts more with the gelatin surface thereby wetting it more. Not wishing to be bound by theory but it is believed the use of the emulsifier (lecithin) facilitates the interaction of the oil phase of the liquid center composition with the immiscible water phase (gelatin coated slide) and reduces the tendency to form droplets, but rather allows for the liquid center composition to spread over the slide. As the liquid center composition wets the gelatin-coated slide it would likewise be expected to wet the oral mucosa of a consumer's mouth.

Example 3

Stability Study

The stability of cube-shaped confectionery products comprising a liquid center composition that is a water-in-oil emulsion was compared to a conventional liquid center-fill hard candy prepared by a rotary molding process under an accelerated aging study. The stability of the samples was evaluated using X-ray tomography which provides clear images of the center and the shell as well as any air bubbles ("voids") that may have occurred either by the forming process or by the degradation of the product.

Three replicas of each product were stored in enclosed glass vials with screw-cap lids and stored for weekly intervals in a 40° C./75% relative humidity stability cabinet until removal for scanning. At time zero and weekly intervals thereafter (1, 2, 3, 4, 6, and 8 weeks) each sample was removed from its container and X-ray tomography images were taken at the three main axes. The conditions during scanning were about 21° C. and about 35-45% relative humidity. The X-ray tomography scan settings can be found in Table 5.

TABLE 5

Image Acquisition:

X-Ray CT scanner (Skyscan 1172), X-Ray beam 50 kV and 201 μA.
Scans were performed with the Skyscan control program (version 1.5 (build 13), A Hamamatsu 10 Mp camera), reconstruction with the Skyscan recon software (version 1.6.4.1)

Sample preparation:

The hard sweet samples were integrally scanned non invasively
Maximum instrument resolution was used (~10 microns @MR and ~23 microns @LR).

Parameter of Scanning:

2000 × 1096 camera pixel, camera pixel size: 11.61 microns
Scan were performed over 180°,
rotation step: 0.2(MR)/0.3(LR) and frame averaging: 6-8
and random movement: 5
Al filter was used.
Scan duration: ~2 hours Parameter of reconstruction:

Setting contrast: 0-0.02 (LR) and 0-0.06 (MR)
Smoothing: 2
ring artifact reduction: 20
beam hardening: 51

Figure 1:
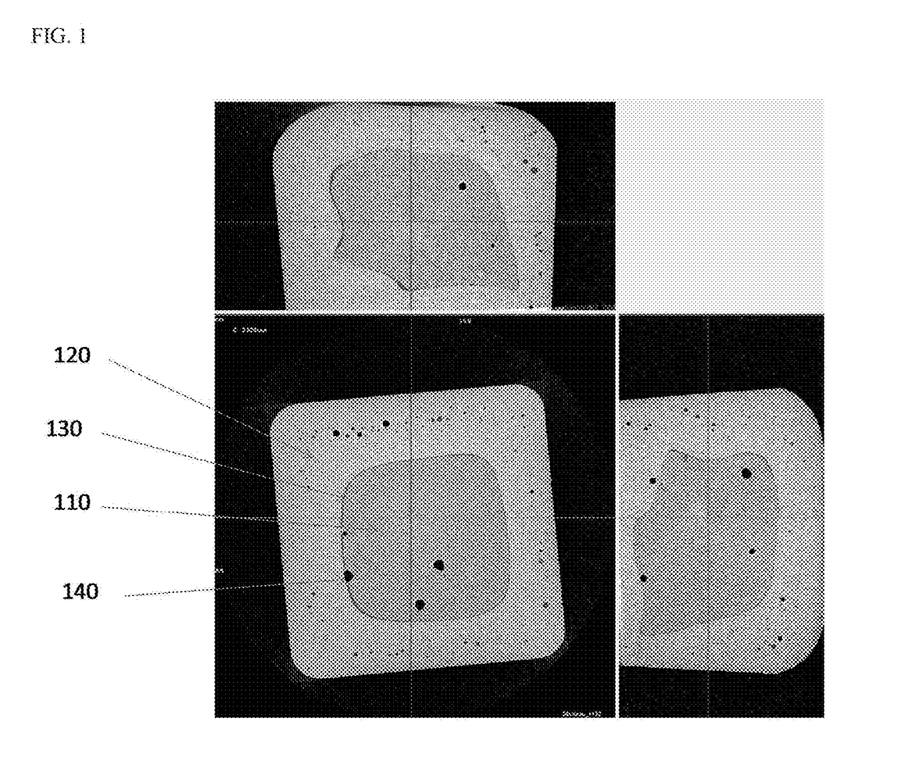
FIG. 1 X-ray tomography image of cube-shaped liquid filled confectionery at time 0 at three major axes.
Figure 2:
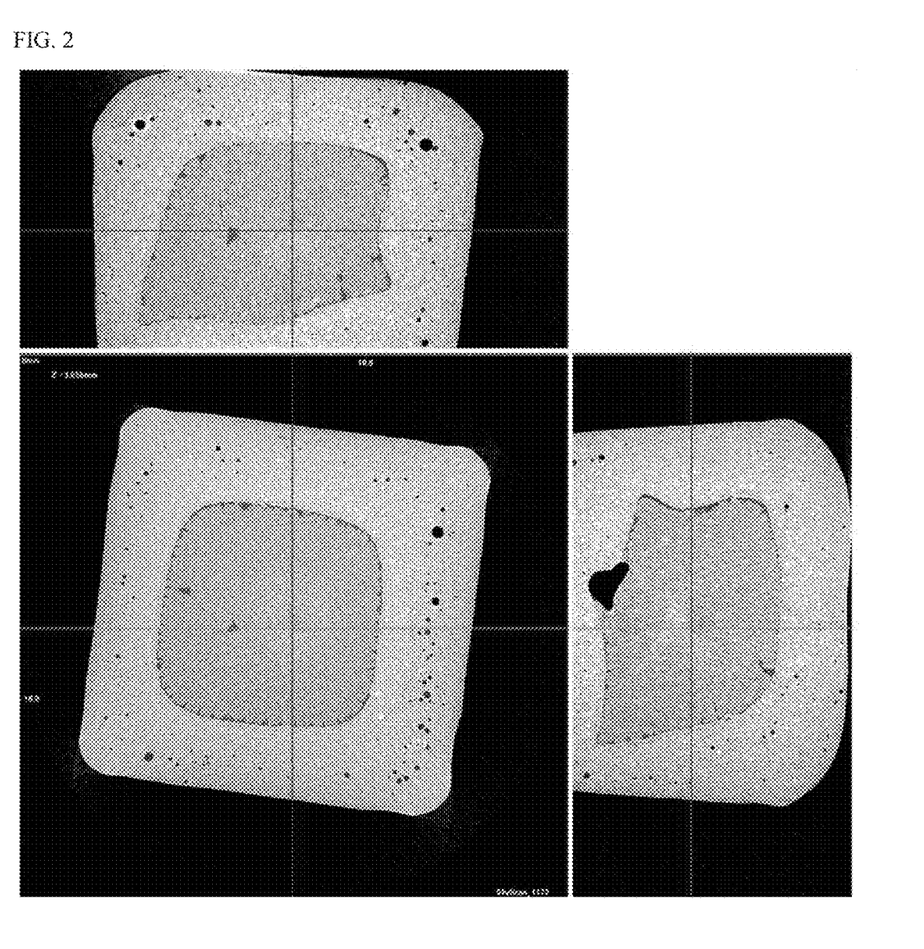
FIG. 2 X-ray tomography image of cube-shaped liquid filled confectionery at time 2 weeks, 40° C. at three major axes.
Figure 3:
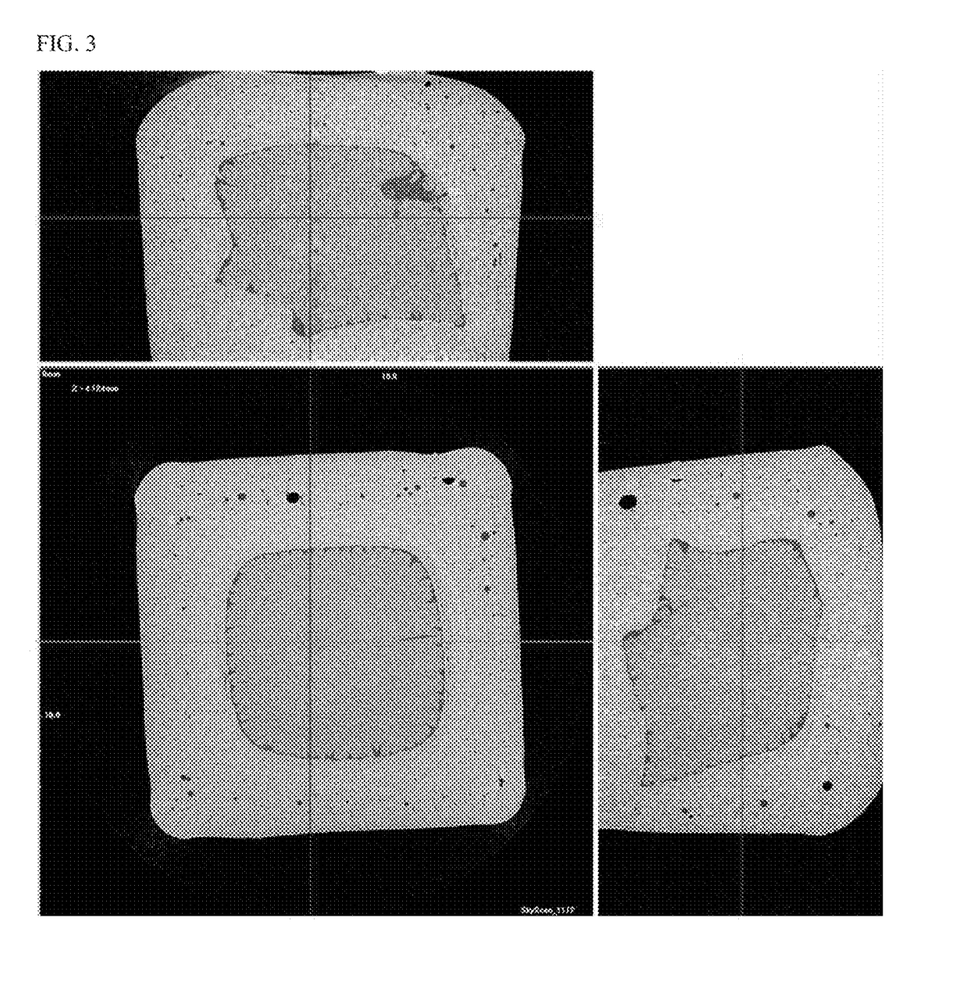
FIG. 3 X-ray tomography image of cube-shaped liquid filled confectionery at time 6 weeks, 40° C. at three major axes.

The confectionery composition of Example 1 (shell Fruit 2, liquid center composition Fruit 2) exhibited no change in the shell thickness as a result of dissolution by the liquid center material between time 0 (FIG. 1), 2 weeks (FIG. 2), 4 weeks, 6 weeks (FIG. 3) and 8 weeks of aging according to the X-ray tomography images. By visual inspection, these samples did not exhibit leakage of the liquid center material through the shell. The image in FIG. 1 clearly shows the liquid center composition (110), hard candy shell (120), the interface between the liquid center composition and the hard candy shell (130), and a dark spot which is an air pocket ("void", 140) in the liquid center composition. The voids of the liquid center composition are not static but rather can move around within the liquid. The dark spots in the X-ray tomography images of the hard candy shell are also voids where there is no hard candy material present.

Figure 4:
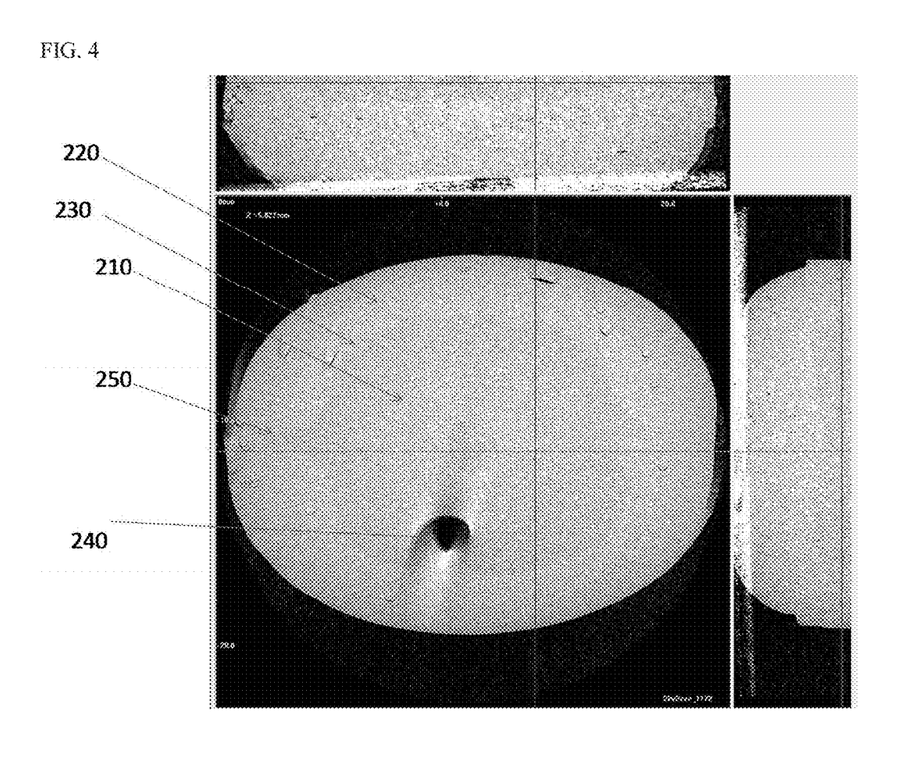
FIG. 4 X-ray tomography image of Comparative liquid center-fill product at time 0 at three major axes.
Figure 5:
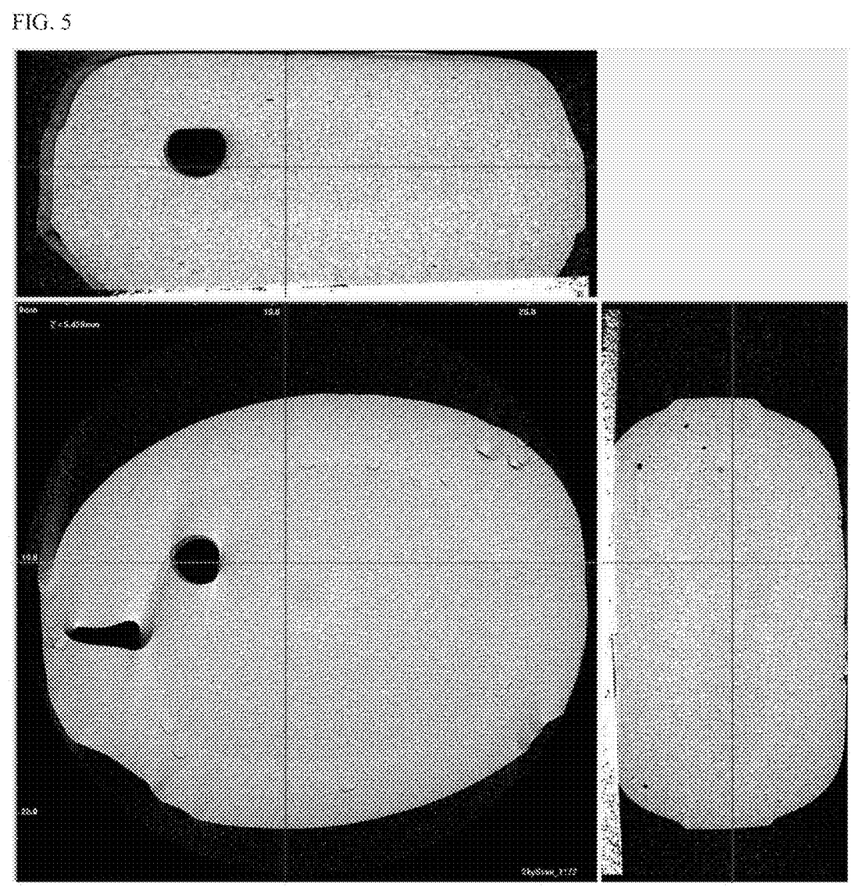
FIG. 5 -ray tomography image of Comparative liquid center-fill product at time 2 weeks, 40° C. at three major axes.
Figure 6:
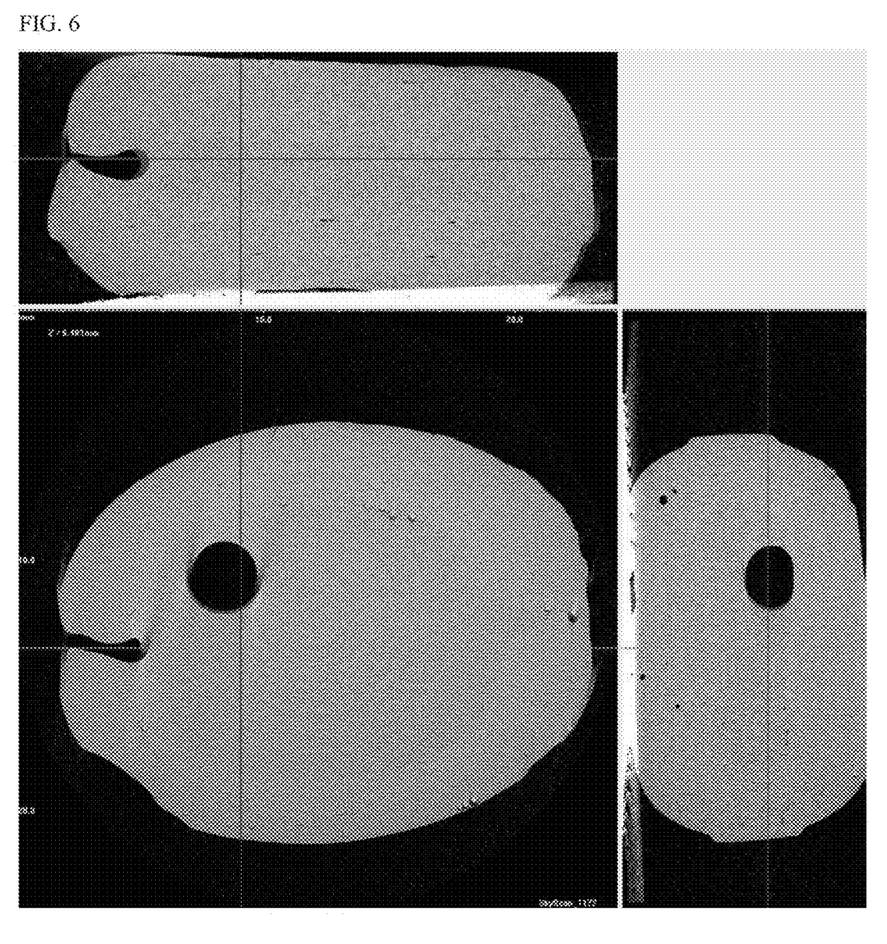
FIG. 6 -ray tomography image of Comparative liquid center-fill product at time 6 weeks, 40° C. at three major axes.

The Comparative conventional liquid center-fill hard candy contains an aqueous-based center-fill material. At time 0, the shell is intact (FIG. 4, center-fill (210), shell (220), interface between the shell and the center-fill (230), air pocket (240)). The location of the seal can be seen in the image of FIG. 4 represented by a protrusion of center-fill material (250). At 2 weeks of aging, clear evidence of shell dissolution can be seen in the X-ray image where there is a large void forming in the shell at the location of the seal (FIG. 5). After 3 weeks the Comparative samples started to leak center-fill through the shell. In FIG. 6 after 6 weeks of aging, a free path through the shell can be seen from where the center-fill originated to the outside edge of the sample. The observed dissolution of the Comparative sample shell occurs predominantly at the thinnest portion of the shell, that is, at the seal formed by the rotary process. A uniform total dissolution of the shell was not observed.

The study shows the superior stability of the deposited product comprising a water-in-oil emulsion as the liquid center-fill. Not wishing to be bound by theory, but it is believed the stability may be due to the combination of the method of forming the product, i.e. without the formation of a seal in the shell as in traditional rotary molding processes, coupled with a center-fill having a low content of water and a higher lipophilic content, which does not appear to dissolve the hard candy shell effectively.

As used herein the terms "comprising" (also "comprises," etc.), "having," and "including" is inclusive (open-ended) and does not exclude additional, unrecited elements or method steps. The singular forms "a," "an," and "the" include plural referents unless the context clearly dictates otherwise. The endpoints of all ranges directed to the same characteristic or component are independently combinable, and inclusive of the recited endpoint. The term "a combination thereof" is inclusive two or more components of the list. The term "homogeneous" refers to a uniform blend of the components. The term "or" means "and/or." Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The terms "first," "second," and the like, "primary," "secondary," and the like, as used herein do not denote any order, quantity, or importance, but rather are used to distinguish one element from another.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A confectionery product, comprising:
    a translucent hard candy shell comprising a first flavorant, and
    a liquid center composition wherein the liquid center composition is a water-in-oil emulsion comprising a second flavorant and a colorant, the liquid center composition is completely surrounded by and is visible through the hard candy shell;
    wherein the liquid center composition has a moisture content of about 0.01 to about 4.0 wt. % based on the total weight of the liquid center composition, and has a contact angle of less than 80 degrees on a gelatin coated surface.

2. The confectionery product of claim 1, wherein the confectionery product weighs 0.5 to 6 grams.

3. The confectionery product of claim 1, wherein the confectionery product is in the shape of a cube, cuboid, hemispherium, circular cone, circular truncated cone, three-sided pyramid, four-sided pyramid, or a multi-sided pyramid.

4. The confectionery product of claim 1, wherein the confectionery product is cube-shaped.

5. The confectionery product of claim 4, wherein the liquid center material does not leak through the hard candy shell after aging the confectionery at 40° C. for 8 weeks at 75% relative humidity.

6. The confectionery product of claim 4, wherein the liquid center composition is substantially free of voids having a cross sectional area greater than 0.5% of the cross sectional area of the confectionery after aging the confectionery for three weeks at 40° C. and 75% relative humidity.

7. The confectionery product of claim 4, wherein the confectionery product is cube-shaped and weighs less than 2 grams and has a distance between opposing walls of less than or equal to 0.5 inch (12.7 mm), and wherein five of six sidewalls are substantially straight and a sixth sidewall is arcuate.

8. The confectionery product of claim 4, wherein the liquid center material is visible through all sides of the hard candy shell.

9. The confectionery product of claim 4, wherein the liquid center composition is about 5 to about 20 wt. % of the total confectionery weight and the confectionery weighs less than 2 grams.

10. The confectionery product of claim 4, wherein the liquid center material is positioned within the hard candy shell such that a distance between any point on a periphery of the liquid center and the nearest point on an outer wall of the hard candy shell is greater than 0.6 mm and there is no void in the path connecting the points that is greater than 20% of the distance.

11. The confectionery product of claim 4, wherein the surface of the confectionery comprises microcrystallization thereby preventing the plurality of confectioneries from adhering to one another in a package and to freely pour out of the package as individual units.

12. The confectionery product of claim 4, wherein the hard candy shell comprises an outer surface which permits free flow of a plurality of confectioneries from a container, wherein the individual units of the plurality have been in direct contact with each other for at least 30 days at STP (25° C., 77° F., 100 kPa, 14.504 psi, 0.986 atm) and 30% to 60% relative humidity.

13. The confectionery product of claim 4, wherein the hard candy shell and the liquid center composition comprise menthol, wherein a ratio of percent menthol in the liquid center composition to that in the hard candy shell is at least 1.5:1.

14. The confectionery product of claim 4, wherein the confectionery provides a first flavor sensation when consumed that is entirely due to the first flavorant of the hard candy shell and a second flavor sensation later in time wherein the second flavor sensation is created by a combination of the first flavorant and the second flavorant of the liquid center composition.

15. The confectionery product of claim 4, wherein the liquid center material provides a different taste experience compared to a taste experience before the liquid center material is released,
wherein upon consumption when a sidewall of the confectionery is breached, a portion of the liquid center material remains attached to an interior hard candy shell surface one minute after breach.

16. The confectionery product of claim 15, wherein at least 20% of the liquid center material remains attached to the interior hard candy shell surface one minute after breach.

17. The confectionery product of claim 4, wherein when the confectionery is consumed
the liquid center material provides a liquid sensation;
the liquid center material is not tasted until at least 20% of the hard candy shell has dissolved; and
the confectionery provides a breath-freshening effect.

18. The confectionery product of claim 4, wherein
the liquid center composition comprises a flavorant, a cooling agent, a warming agent, a tingling agent, an acid, a high intensity sweetener, a functional ingredient, or a combination thereof; and
the hard candy shell comprises a flavorant, a sensate, an acid, a high intensity sweetener, a functional ingredient, a glitter or speckles, or a combination thereof.

19. The confectionery product of claim 4, wherein the confectionery is about 0.5 to about 2 grams in weight; and
has a cube-shape having rounded edges and no sharp edges.

20. The confectionery product of claim 4, wherein the first flavor and the second flavorant are the same or different.

21. The confectionery product of claim 4, wherein the hard candy shell comprises isomalt.

22. The confectionery product of claim 4, wherein the liquid center composition comprises medium chain triglycerides, glycerin, lecithin, and sugar polyol.

23. The confectionery product of claim 4, wherein the liquid center composition comprises medium chain triglycerides, hydrogenated vegetable oil, glycerin, lecithin, and sugar polyol.

24. The confectionery product of claim 4, wherein the liquid center composition comprises medium chain triglycerides, sucrose fatty acid ester, glycerin, lecithin, and sugar polyol.

25. The confectionery product of claim 4, wherein the liquid center composition has a contact angle of about 10 to about 70 degrees on a gelatin coated surface.

26. A package, comprising:
a plurality of deposited confectionery products,
the deposited confectionery comprising
a translucent hard candy shell comprising a first flavorant, and
a liquid center composition wherein the liquid center composition is a water-in-oil emulsion comprising a second flavorant and a colorant, the liquid center composition is completely surrounded by and is visible through the hard candy shell, wherein the liquid center composition has a moisture content of about 0.01 to about 4.0 wt. % based on the total weight of the liquid center composition, and has a contact angle of less than 80 degrees on a gelatin coated surface;
wherein each unit of the plurality is individually unwrapped; and
wherein the package comprises a moisture barrier overwrap.

* * * * *